1

(12) United States Patent
Ootake et al.

(10) Patent No.: US 8,084,499 B2
(45) Date of Patent: Dec. 27, 2011

(54) MODIFIED CLAY MINERAL

(75) Inventors: Souichirou Ootake, Kawasaki (JP);
Yoshihisa Imori, Kawasaki (JP);
Tetsuya Izumi, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 356 days.

(21) Appl. No.: 12/241,494

(22) Filed: Sep. 30, 2008

(65) Prior Publication Data

US 2009/0098169 A1   Apr. 16, 2009

Related U.S. Application Data

(63) Continuation of application No. PCT/JP2007/057520, filed on Mar. 28, 2007.

(30) Foreign Application Priority Data

Mar. 30, 2006   (JP) .................................. 2006-093678

(51) Int. Cl.
*A61K 31/215* (2006.01)
*A61K 31/216* (2006.01)
*A61K 31/22* (2006.01)
*A61K 31/223* (2006.01)
*A61K 8/06* (2006.01)
*A61K 8/25* (2006.01)
*A61K 8/44* (2006.01)

(52) U.S. Cl. ......... 514/538; 514/551; 514/770; 514/938

(58) Field of Classification Search .................. 514/542, 514/938, 538, 551, 770
See application file for complete search history.

(56) References Cited

U.S. PATENT DOCUMENTS 5,474,778 A * 12/1995 Ichikawa et al. .............. 424/401
2004/0175350 A1 * 9/2004 Urgell Beltran et al. .. 424/70.27

FOREIGN PATENT DOCUMENTS

| JP | 7-101824 | 4/1995 |
| JP | 9-2816 | 1/1997 |
| JP | 2003-81755 | 3/2003 |
| JP | 2004-292347 | 10/2004 |
| JP | 2004-359483 | 12/2004 |

* cited by examiner

*Primary Examiner* — John Pak
(74) *Attorney, Agent, or Firm* — Oblon, Spivak, McClelland, Maier & Neustadt, L.L.P.

(57) ABSTRACT

Modified clay minerals obtained by treating a clay mineral with a particular acylarginine derivative are useful for stabilizing emulsion compositions, inter alia, W/O emulsion composition, while hardly causing skin irritation, and providing moisture retention properties.

12 Claims, No Drawings

MODIFIED CLAY MINERAL

CROSS REFERENCES TO RELATED APPLICATIONS

This application is a continuation of International Patent Application No. PCT/JP2007/057520, filed on Mar. 28, 2007, and claims priority to Japanese Patent Application No. 2006-093678, filed on Mar. 30, 2006, both of which are incorporated herein by reference in their entireties.

BACKGROUND OF THE INVENTION

1. Field of the Invention

The present invention relates to modified clay minerals. The present invention further relates to emulsion compositions which contain such a modified clay mineral.

2. Discussion of the Background

Emulsion compositions include W/O type (water-in-oil type) compositions and O/W type (oil-in-water type) compositions. Generally, W/O emulsion compositions have poor emulsion stability as compared to O/W emulsion compositions and tend to permit easy separation of an oil solution from water, particularly when they have low viscosity. Thus, there have been attempts to enhance the emulsion stability (temperature stability) of W/O emulsion compositions.

Japanese Patent Application Publication No. JP-A-61-129033 proposes a method of stabilizing a water-in-oil emulsion composition by the use of, as an emulsifying aid, an organic modified clay mineral obtained by treating a water swellable clay mineral with a quaternized ammonium salt type cationic surfactant and a non-ionic surfactant. Although an apparent stabilizing effect is obtained, the composition causes skin irritation when used as an emulsion composition, since the quaternized ammonium salt type cationic surfactant used for treating the organic modified clay mineral remains. In addition, the composition is not entirely satisfactory from the aspect of moisture retention property.

Accordingly, there is a high demand for a material that provides an emulsion stabilizing effect on an emulsion composition, inter alia, a W/O emulsion composition, hardly causes skin irritation, and provides a moisture retention property.

SUMMARY OF THE INVENTION

Accordingly, it is one object of the present invention to provide novel materials which provide an emulsion stabilizing effect on an emulsion composition.

It is another object of the present invention to provide novel materials which provide an emulsion stabilizing effect on an emulsion composition, such as a W/O emulsion composition.

It is another object of the present invention to provided novel materials which provide an emulsion stabilizing effect on an emulsion composition and which hardly cause skin irritation.

It is another object of the present invention to provided novel materials which provide an emulsion stabilizing effect on an emulsion composition and which provide improved moisture retention.

It is another object of the present invention to provide novel processes for making such a material.

It is another object of the present invention to provide novel emulsions which contain such a material.

It is another object of the present invention to provide novel processes for making such an emulsion.

These and other objects, which will become apparent during the following detailed description, have been achieved by the inventors' discovery that the above-mentioned objects can be obtained by a modified clay mineral obtained by treating a clay mineral with a particular acylarginine derivative.

Accordingly, the present invention provides the following:

(1) A modified clay mineral, which is prepared by treating a clay mineral with a compound represented by the following formula (1):

$$R^1\text{-NH-CH(COOR}^2\text{)-CH}_2\text{-CH}_2\text{-CH}_2\text{-NH-C(NH}_2\text{)=NH}_2^+ \; Y^- \tag{1}$$

wherein $R^1$ is an acyl group, $R^2$ is an alkyl group and $Y^-$ is an anion derived from an organic acid or an inorganic acid.

(2) The modified clay mineral of (1), wherein $R^1$ of the compound represented by the above-mentioned formula (1) is a saturated or unsaturated, straight chain or a branched chain acyl group having 12 to 18 carbon atoms.

(3) An emulsion composition, which comprises the modified clay mineral of any of (1) and (2).

(4) An emulsion composition, which comprises a clay mineral and a compound represented by the above-mentioned formula (1).

(5) The composition of any of (3) and (4), wherein the emulsion composition is a cosmetic composition.

(6) The composition of any of (3) to (5), further comprising acyl acidic amino acid ester.

Thus, the present invention provides a modified clay mineral that provides an emulsion stabilizing effect on an emulsion composition, hardly causes skin irritation, and provides a moisture retention property, as well as an emulsion composition that shows emulsion stabilizing effect, hardly causes skin irritation, and has a moisture retention property, by containing the modified clay mineral.

DETAILED DESCRIPTION OF THE PREFERRED EMBODIMENTS

The modified clay mineral of the present invention can be obtained by treating clay mineral with a compound represented by the formula (1). It is sequentially explained in the following.

The clay mineral to be used in the present invention is not particularly limited as long as it contains, as a main component, a silicate mineral having a layer-like crystal structure. Examples thereof include smectite, bentonite, montmorillonite, saponite, hectorite and the like. Since a good emulsion stabilizing effect and versatility can be afforded, bentonite, montmorillonite, saponite and hectorite are preferable, bentonite and montmorillonite are more preferable, and montmorillonite is particularly preferable. These may be naturally occurring or synthetic. These clay minerals may be used alone or in a mixture of two or more kinds thereof.

The acylarginine derivative to be used in the present invention is a compound represented by the following formula (1):

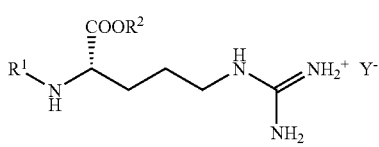

(1)

In the above-mentioned formula (1), $R^1$ is an acyl group and is not particularly limited. However, it is preferably a straight chain or branched chain fatty-acid residue (carboxylic acid free of OH) having 8 to 30 carbon atoms, more preferably a straight chain or branched chain fatty-acid residue having 8 to 20 carbon atoms. Specifically, an acyl group such as a lauric acid residue (a lauroyl group), a palmitic acid residue (a palmitoyl group), a myristic acid residue (a myristoyl group), a stearic acid residue (a stearoyl group), an oleic acid residue (an oleoyl group), a linoleic acid residue (a linoleoyl group), a linolenic acid residue (a linolenoyl group), a coconut oil fatty-acid residue, a palm oil fatty-acid residue, and the like can be mentioned. Since not only the emulsion stabilizing effect but also the moisture retention properties are high, a lauric acid residue and a coconut oil fatty-acid residue are preferable, and a coconut oil fatty-acid residue is more preferable.

In the above-mentioned formula (1), $R^2$ is an alkyl group and is not particularly limited. However, it is preferably a straight chain or branched chain alkyl group having 1 to 10 carbon atoms, more preferably a straight chain or branched chain alkyl group having 2 to 5 carbon atoms. Specifically, a methyl group, an ethyl group, a propyl group, an isopropyl group, an s-propyl group, a butyl group, an isobutyl group, an s-butyl group, a t-butyl group, a pentyl group, a hexyl group, a heptyl group, an octyl group, a 2-ethylhexyl group, a nonyl group, an isononyl group, a decyl group, and the like can be mentioned. Of these alkyl groups, an ethyl group, an isopropyl group, an isobutyl group, and an s-butyl group are preferable; an ethyl group and an isopropyl group are more preferable; and an ethyl group is particularly preferable.

In the above-mentioned formula (1), $Y^-$ is an anion, and an anion derived from an organic acid such as citric acid, lactic acid, glutamic acid, pyrrolidone carboxylic acid, aspartic acid and the like; an anion derived from an inorganic acid such as hydrogen chloride, sulfuric acid, nitric acid and the like; and the like can be mentioned. Among these, an anion derived from glutamic acid, an anion derived from pyrrolidone carboxylic acid, an anion derived from aspartic acid and an anion derived from hydrogen chloride (chlorine ion) are preferable, and an anion derived from pyrrolidone carboxylic acid is more preferable.

In the compound represented by the above-mentioned formula (1), cation refers to that portion of the compound of formula (1) other than $Y^-$, and is not particularly limited. However, it is preferably N-cocoylarginine ethyl ester cation, N-cocoylarginine isopropyl ester cation, N-cocoylarginine isobutyl ester cation, N-cocoylarginine s-butyl ester cation, N-lauroylarginine ethyl ester cation, N-lauroylarginine isopropyl ester cation, N-lauroylarginine isobutyl ester cation, N-lauroylarginine s-butyl ester cation, N-palmitoylarginine ethyl ester cation, N-stearoylarginine ethyl ester cation, N-oleylarginine ethyl ester cation, and the like can be mentioned. Since not only an emulsion stabilizing effect but also moisture retention properties are high, N-cocoylarginine ethyl ester cation, N-cocoylarginine isopropyl ester cation, N-lauroylarginine ethyl ester cation, and N-lauroylarginine isopropyl ester cation are more preferable, and N-cocoylarginine ethyl ester cation and N-lauroylarginine ethyl ester cation are particularly preferable.

More preferable specific examples of the compound represented by the above-mentioned formula (1) include cocoylarginine ethyl pyrrolidone carboxylate, cocoylarginine ethyl glutamate, cocoylarginine ethylhydrochloride, cocoylarginine isopropyl pyrrolidone carboxylate, cocoylarginine isobutyl pyrrolidone carboxylate, lauroylarginine ethyl pyrrolidone carboxylate, lauroylarginine isopropyl glutamate, lauroylarginine isobutyl hydrochloride, and the like. Since not only an emulsion stabilizing effect but also moisture retention properties are high, cocoylarginine ethyl pyrrolidone carboxylate, cocoylarginine ethyl glutamate, cocoylarginine ethyl hydrochloride and cocoylarginine isopropyl pyrrolidone carboxylate are preferable, cocoylarginine ethyl pyrrolidone carboxylate, cocoylarginine ethyl glutamate, and cocoylarginine ethyl hydrochloride are more preferable; cocoylarginine ethyl pyrrolidone carboxylate and cocoylarginine ethyl hydrochloride are even more preferable; and cocoylarginine ethyl pyrrolidone carboxylate is particularly preferable.

As a treatment method to afford the modified clay mineral of the present invention, for example, a method including dissolving or dispersing a clay mineral and a compound represented by the above-mentioned formula (1) in water, and sufficiently stirring (e.g., powerful stirring by a disper and the like etc.) the mixture and the like can be mentioned. A desired clay mineral can be obtained by treating a clay mineral and a compound represented by the formula (1) at a weight ratio of 1:10 to 10:1, preferably 1:4 to 4:1.

While the modified clay mineral of the present invention can be added to, for example, cosmetic, the modified clay mineral may be formed in the system (in situ) by blending one or more components other than the modified clay mineral used for constituting the above-mentioned cosmetic, a clay mineral before modification and a compound represented by the above-mentioned formula (1) to prepare a cosmetic. In this case, a clay mineral is dispersed in an oil layer, a compound represented by the formula (1) is dissolved in an aqueous layer, and then the oil layer and the aqueous layer are mixed to give an emulsion composition. A desired cosmetic can be obtained by processing such that the clay mineral and the compound represented by the formula (1) are present at a weight ratio of 1:10 to 10:1, preferably 1:4 to 4:1.

An emulsion composition that shows emulsion stabilizing effect, hardly causes skin irritation, and has moisture retention property can be provided by adding the modified clay mineral of the present invention to an emulsion composition comprising water and oil solution. While the emulsion composition can take any form of a W/O emulsion composition and an O/W emulsion composition, the effect of the present invention becomes more remarkable for a W/O emulsion composition with comparatively poor emulsion stability. As mentioned above, since the emulsion composition can take any form of a W/O emulsion composition and an O/W emulsion composition, the amount of the water and oil solution in the emulsion composition is not particularly limited, and can be appropriately set according to the use, function and the like of the emulsion composition. The emulsion composition to be used here refers to a composition consisting of water and an oil solution in a narrow sense, and a composition comprising water, an oil solution and other additive within a range that does not inhibit the effect in a wide sense.

While the amount of the modified clay mineral relative to the whole emulsion composition of the present invention is not particularly limited, it may be added at a proportion of 0.001 percent by mass to 10.0 percent by mass, based on the total mass of the emulsion. When the amount of the modified clay mineral in the emulsion composition is less than 0.001 percent by mass, the emulsion stability improving effect and thickening effect on the emulsion composition may become small. When it is greater than 10.0 percent by mass, the viscosity of the emulsion composition may become too high. Since the effects of emulsion stability and moisture retention property can be effectively exerted on the emulsion composition without an influence of other components, the lower limit of the amount of the modified clay mineral is preferably 0.01 percent by mass, more preferably 0.1 percent by mass, still more preferably 0.2 percent by mass, still more preferably 0.5 percent by mass, particularly preferably 1.0 percent by mass, based on the total mass of the emulsion. Since appropriate viscosity of the emulsion composition can be achieved, the upper limit is preferably 10.0 percent by mass, more preferably 7.0 percent by mass, still more preferably 5.0 percent by mass, based on the total mass of the emulsion.

The emulsion composition of the present invention can be used for various cosmetics. Specifically, skin external preparation such as facial wash creams, cleansing foams, cleansing creams, massage creams, cold creams, moisture creams, skin milks, skin lotions, hand creams, facial masks, cosmetics for men's skin, foundations, lip rouges, pressed powders, eye shadows, body shampoos, solid soaps, liquid detergents, antiperspirants, after shaving creams, sunscreen preparations, bath agents, external pharmaceutical compositions, and the like; hair cosmetics such as shampoos, rinses, hair-growth drugs, treatments, conditioners, tic agents, hair liquids, set lotions, permanent wave solutions, hair creams, hair lotions, hair mousse, perm solutions, hair dyes, hair colorings, hair manicures, etc.; and the like can be mentioned. Of these, since the skin irritation is rare and moisture retention property is high, a skin external preparation is preferable, and a sunscreen preparation is particularly preferable.

In addition, sunscreen preparations are preferably in the form of O/W emulsion compositions to ensure good usability. On the other hand, to enhance UV protection ability, the form of a W/O emulsion composition is preferable. For a sunscreen preparation, the amount of an oil solution is desirably not less than 10 percent by mass, more preferably not less than 30 percent by mass, and not more than 90 percent by mass, more preferably not more than 70 percent by mass, based on the total weight of the composition. The amount of water is desirably not less than 5 percent by mass, more preferably not less than 30 percent by mass, and not more than 80 percent by mass, more preferably not more than 50 percent by mass, based on the total mass of the composition.

The viscosity of the sunscreen preparation is particularly preferably not less than 100 mPa·s, more preferably not less than 500 mPa·s, and preferably not more than 30000 mPa·s, more preferably not more than 10000 mPa·s. A sunscreen preparation having such viscosity can be prepared by blending the above-mentioned preferable amounts of a modified clay mineral, an oil solution, water, and the like.

An oil solution for the emulsion composition of the present invention, and a cosmetic using the emulsion composition may be any of a natural oil and a synthetic oil as long as it is a known oil solution used for ordinary cosmetics, quasi-drugs, external pharmaceutical products and the like, and may be any of a solid, a semisolid, and a liquid. Specifically, various oil solutions such as hydrocarbons, waxes, animal oil, lanolin and a derivative thereof, fatty acids, higher alcohol, ester oil, glyceride oil, silicone oil, fluorine oil solution, and the like can be used.

Examples of the hydrocarbons include ozocerite, squalane, squalene, ceresin, paraffin, paraffin wax, liquid paraffin, pristane, polyisobutylene, microcrystalline wax, petrolatum, and the like. Examples of the wax include beeswax, Carnauba wax, candelilla wax, whale wax, and the like. Examples of the animal oil include beef fat, hoof oil, beef bone oil, hardened beef tallow, hydrogenated oil, turtle oil, lard, horse fat, mink oil, liver oil, egg-yolk oil, and the like.

Examples of the lanolin and a derivative thereof include lanolin, liquid lanolin, reduced lanolin, lanolin alcohol, hard lanolin, lanolin acetate, lanolin fatty acid isopropyl, POE (polyoxyethylene, hereinafter the same) lanolin alcohol ether, POE lanolin alcohol acetate, lanolin fatty acid polyethylene glycol, POE hydrogenated lanolin alcohol ether, and the like. Examples of the fatty acids include lauric acid, myristic acid, palmitic acid, stearic acid, behenic acid, undecylenoic acid, oleic acid, arachidonic acid, docosahexaenoic acid (DHA), isostearic acid, 12-hydroxystearic acid, and the like.

Examples of the higher alcohol include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterol, sitosterol, lanosterol, POE cholesterol ether, monostearyl glycerol ether (batyl alcohol), and the like.

Examples of the ester oil include diisobutyl adipate, 2-hexyldecyl adipate, di-2-heptylundecyl adipate, N-alkylglycol monoisostearate, isocetyl isostearate, trimethylolpropane triisostearate, di-2-ethylhexane acid ethylene glycol, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, dicapric acid neopentyl glycol, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, N-lauroyl-L-glutamic acid-2-octyldodecyl ester, diisostearyl malate, and the like.

Examples of the glyceride oil include acetoglyceride, glyceride triisooctanoate, glyceride triisostearate, glyceride triisopalmitate, glyceride tri-2-ethylhexanoate, glyceride monostearate, glyceride di-2-heptylundecanoate, glyceride trimyristate, and the like. Examples of the silicone oil include higher alkoxide-modified silicone such as dimethylpolysiloxane, methylphenylpolysiloxane, methyl hydrogen polysiloxane, octamethylcyclotetrasiloxane, decamethylcyclopentasiloxane, dodecamethylcyclohexasiloxane, tetramethyltetrahydrogencyclotetrasiloxane, stearoxy silicone, and the like, higher fatty acid-modified silicone, silicone resin, silicon rubber, and the like. Examples of the fluorine oil solution include perfluoropolyether, perfluorodecalin, perfluorooctane, and the like.

The emulsion composition of the present invention and cosmetics using the emulsion composition may contain, besides the above-mentioned modified clay mineral, oil solution and water, various known additives that are added, as necessary, to general cosmetics and preparations such as quasi-drugs, external pharmaceutical products and the like, as long as the effect of the invention is not inhibited. Examples of such additives include surfactants, metal soaps, gelling agents, powders (including pigments), lower alcohols, moisturizing agents, water-soluble polymers, film forming agents, resins, UV protecting agents, inclusion compounds, antibacterial agents, flavors, deodorants, salts, pH adjusters, algefacients, animal·microorganism-derived extracts, plant extracts, whitening agents, blood circulation promoters, astringents, antiseborrheic agents, anti-inflammatory agents, active oxygen elimination agents, antioxidants, stratum corneum dissolving agents, enzymes, thickeners (excluding the modified clay mineral of the present invention), and the like.

Examples of the surfactant include fatty acid soaps such as sodium stearate, triethanolamine palmitate and the like, carboxylic acid salts such as alkylethercarboxylic acid and a salt thereof, condensation of amino acid and fatty acid, and the like, sulfuric acid ester salts such as alkylsulfonate, alkenesulfonate, sulfonate of fatty acid ester, sulfonate of fatty acid amide, alkylsulfonate, alkylsulfuric acid ester salts, secondary higher alcohol sulfuric acid ester salts, alkyl and allylethersulfuric acid ester salts, sulfuric acid ester salts of fatty acid ester, sulfuric acid ester salts of fatty acid alkylolamide, turkey red oil and the like, anionic surfactant such as alkylphosphate, ether phosphate, alkylallyletherphosphate, amidephosphate, N-acylamino acid activating agent and the like; amine salt such as alkylamine salt, polyamine and amino alcohol fatty acid derivative and the like, cationic surfactant such as pyridinium salt, imidazolium salt and the like; nonionic surfactant such as sorbitan fatty acid ester, glycerol fatty acid ester, polyglycerin fatty acid ester, propylene glycol fatty acid ester, polyethylene glycol fatty acid ester, sucrose fatty acid ester, polyoxyethylene alkyl ether, polyoxypropylene alkyl ether, polyoxyethylene alkylphenyl ether, polyoxyethylene fatty acid ester, sorbitan polyoxyethylene fatty acid ester, polyoxyethylene sorbitol fatty acid ester, polyoxyethylene glycerol fatty acid ester, polyoxyethylene propylene glycol fatty acid ester, polyoxyethylene castor oil, polyoxyethylene hydrogenated castor oil, polyoxyethylenephytostanol ether, polyoxyethylenephytosterol ether, polyoxyethylenecholestanol ether, polyoxyethylenechlesteryl ether, polyoxyalkylene-modified organopolysiloxane, polyoxyalkylene·alkyl-comodified organopolysiloxane, alkanol amide, sugar ether, sugar amide and the like; ampholytic surfactant such as betaine, aminocarboxylate, imidazoline derivative and the like.

Examples of the metal soaps include 12-hydroxyaluminum stearate, zinc stearate, aluminum stearate, calcium stearate, magnesium stearate, zinc myristate, magnesium myristate, cetyl phosphoric acid zinc, cetyl calcium phosphate, cetyl phosphoric acid zinc sodium, zinc laurate, undecylenoic acid zinc, and the like. Examples of the gelling agent include amino acid derivatives (N-lauroyl-L-glutamic acid, α,γ-di-n-butylamine, etc.), dextrin fatty acid ester (dextrin palmitic acid ester, dextrin stearic acid ester, dextrin 2-ethylhexane acid palmitic acid ester, etc.), sucrose fatty acid ester (sucrose palmitic acid ester, sucrose stearic acid ester etc.), benzylidene derivative of sorbitol (monobenzylidenesorbitol, dibenzylidenesorbitol etc.) and the like.

As the powder, any can be used irrespective of shape (spherical, needle, plate, etc.), particle size (fumy, fine particles, pigment level, etc.), and particles structure (porous, non-porous, etc.) thereof as long as it is used for general cosmetics. The above-mentioned powder includes inorganic powder, organic powder, colored pigment, pearl pigment, metal powder pigment, tar pigment, natural dye, and the like. Examples of the inorganic powder include magnesium oxide, barium sulfate, calcium sulfate, magnesium sulfate, calcium carbonate, magnesium carbonate, talc, synthetic mica, mica, kaolin, cericite, white mica, synthetic mica, bronze mica, rouge mica, black mica, lithia mica, silicic acid, silicic anhydride, aluminum silicate, magnesium silicate, aluminum silicate magnesium, calcium silicate, barium silicate, stronthium silicate, tungsten acid metal salt, hydroxyapatite, vermiculite, hidirite, montmorillonite, zeolite, ceramic powder, secondary calcium phosphate, alumina, aluminum hydroxide, boron nitride, and the like. Examples of the organic powder include polyamide powder, polyester powder, polyethylene powder, polypropylene powder, polystyrene powder, polyurethane, benzoguanamine powder, polymethylbenzoguanamine powder, tetrafluoroethylene powder, polymethylmethacrylate powder, silk powder, nylon powder, 12 nylon, 6 nylon, styrene acrylic acid copolymer, divinylbenzene·styrene copolymer, vinyl resin, urea resin, phenol resin, fluorine resin, silicon resin, acrylic resin, melamine resin, epoxy resin, polycarbonate resin, microcrystalline fiber powder, lauroyllysine, and the like. Examples of the colored pigment include inorganic red pigments (iron oxide, iron hydroxide, ilmenite), inorganic brown pigments (γ-iron oxide etc.), inorganic yellow pigments (yellow iron oxide, yellow ocher etc.), inorganic black pigments (black iron oxide, carbon black etc.), inorganic violet pigments (manganese violet, cobalt violet etc.), inorganic green pigments (chromium hydroxide, chromium oxide, cobalt oxide, titanium acid cobalt etc.), inorganic blue pigments (iron blue, ultramarine blue etc.), laked tar dye, laked natural dye, and composited powder of these powders, and the like. Examples of the pearl pigment include titanium oxide-coated mica, titanium oxide-coated mica, bismuth oxychloride, titanium oxide-coated bismuth oxychlorise, titanium oxide-coated talc, argentine, titanium oxide-coated colored mica, and the like. Examples of the metal powder pigment include aluminum powder, copper powder, stainless powder, and the like. Examples of the tar pigment include Food Red No. 3, Food Red No. 104, Food Red No. 106, Food Red No. 201, Food Red No. 202, Food Red No. 204, Food Red No. 205, Food Red No. 220, Food Red No. 226, Food Red No. 227, Food Red No. 228, Food Red No. 230, Food Red No. 401, Food Red No. 505, Food Yellow No. 4, Food Yellow No. yellow 5, Food Yellow No. 202, Food Yellow No. 203, Food Yellow No. 204, Food Yellow No. 401, Food Blue No. 1, Food Blue No. 2, Food Blue No. 201, Food Blue No. 404, Food Green No. 3, Food Green No. 201, Food Green No. 204, Food Green No. 205, Food Orange No. 201, Food Orange No. 203, Food Orange No. 204, Food Orange No. 206, Food Orange No. 207, and the like. Examples of the natural dye include carminic acid, laccaic acid, carthamin, brazilin, crocin, and the like. Plural species of the above-mentioned respective powders may be processed into a composite, or subjected to a surface treatment with an oil solution, silicone or fluorine compound etc.

Examples of the lower alcohol include alcohol having 1 to 5 carbon atoms such as ethanol, isopropanol, and the like.

Examples of the moisturizing agent include polyvalent alcohol (glycerol, diglycerol, ethylene glycol, diethylene glycol, triethylene glycol, propylene glycol, dipropylene glycol, 1,3-butylene glycol, polyethylene glycol etc.); amino acids (valine, leucine, isoleucine, alanine, arginine, glutamine, lysine, aspartic acid, glutamic acid, proline, cysteine, cystine, threonine, methionine, histidine, phenylalanine, tyrosine, tryptophan, asparagine, glycine, serine); amino acid derivatives; glycine betaine; dipeptide; tripeptide; and the like. Acyl acidic amino acid esters are particularly preferably as moisturizing agents. Specific examples thereof include N-lauroyl-L-glutamic acid di(cholesteryl·behenyl·octyldodecyl), N-lauroyl-L-glutamic acid di(cholesteryl·octyldodecyl), N-lauroyl-L-glutamic acid di(phytosteryl·behenyl·octyldodecyl), N-lauroyl-L-glutamic acid di(phytosteryl·octyldodecyl), and lauroylsarcosine isopropyl.

Examples of the aqueous polymer include plant polymers (gum arabic, tragacanth, galactan, locust bean gum, guar gum, caraya gum, carageenan, pectin, agar, algecolloid, trant gum, locust bean gum, garactomannan etc.), microorganism polymers (xanthan gum, dextran, succinoglycan, pullulan etc.), animal polymers (casein, albumin, gelatin etc.), starch polymers (starch, carboxymethylstarch, methylhydroxypropylstarch etc.), cellulose polymers (methylcellulose, ethylcellulose, methylhydroxypropylcellulose, carboxymethylcellulose, hydroxymethylcellulose, hydroxypropylcellulose, nitrocellulose, cellulose sodium sulfate, sodium carboxymethylcellulose, crystalline cellulose, cellulose powder etc.), alginic acid polymers (sodium alginate, alginic acid propylene glycol ester etc.), vinyl polymers (polyvinyl methylether, carboxyvinyl polymer, alkylde-modified carboxyvinyl polymer etc.), polyoxyethylene polymers, polyoxyethylenepolyoxypropylene copolymer polymers, acrylic polymer (sodium polyacrylate, polyethylacrylate, polyacrylamide etc.), polyethyleneimine, cationic polymer, inorganic water-soluble polymer and the like. In addition, they also include film forming agents such as polyvinyl alcohol, polyvinyl pyrrolidone and the like.

Examples of the UV protection agent include cinnamic acid UV absorbers (paramethoxy cinnamic acid-2-ethylhexyl, isopropyl paramethoxy cinnamate, diethanolamine paramethoxy cinnamate, diparamethoxy cinnamic acidmono-2-ethylhexanoic acid glyceril, octyl methoxy cinnamate, methyl diisopropyl cinnamate etc.), benzophenone UV absorbers (2-hydroxy-4-methoxybenzophenone, 2-hydroxy-4-methoxybenzophenone-5-sulfuric acid, 2-hydroxy-4-methoxybenzophenone-5-sodium sulfate, 2,4-dihydroxybenzophenone, 2,2'-dihydroxy-4,4'-dimethoxybenzophenone, 2,2'-dihydroxy-4-methoxybenzophenone, 2,2',4,4'-tetrahydroxybenzophenone, 2-hydroxy-4-n-octoxybenzophenone etc.), benzoic acid UV absorbers (paraminobenzoic acid, ethyl paraminobenzoate, butyl paraminobenzoate, 2-ethylhexyl paradimethylaminobenzoate, glyceril paraminobenzoate, amyl paraminobenzoate etc.), salicylic acid UV absorbers (2-ethylhexyl salicylate, triethanolamine salicylate, homomethyl salicylate, dipropylene glycol salicylate, methyl salicylate, ethylene glycol salicylate, phenyl salicylate, amyl salicylate, benzyl salicylate, isopropylbenzyl salicylate, potassium salicylate etc.), dibenzoylmethane UV absorbers (4-t-butyl-4'-methoxydibenzoylmethane, 4-isopropyldibenzoylmethane, 4-methoxydibenzoylmethane, 4-t-butyl-4'-hydroxydibenzoylmethane etc.), menthyl-O-aminobenzoate, 2-phenyl-benzimidazole-5-sulfuric acid, 2-phenyl-5-methylbenzoxazole, 3-(4-methylbenzylidene)camphor, 2-ethylhexyl-2-cyano-3,3-diphenylacrylate, 2-ethyl-2-cyano-3,3'-diphenylacrylate, 2-(2'-hydroxy-5-methylphenyl)benzotriazole, anthranic acid UV absorbers (menthyl anthranate etc.), urocanic acid UV absorbers (ethyl urocanoate etc.), titanium oxide, zirconium oxide, cerium oxide, zinc oxide, and the like.

Examples of the antibacterial agent include benzoic acid, sodium benzoate, carbolic acid, sorbic acid, potassium sorbate, paraoxybenzoate, parachlorometacresol, hexachlorophene, benzalkonium chloride, chlorhexidine chloride, trichloro carbanilide, photosensitizer, bis(2-pyridylthio-1-oxide)zinc, phenoxyethanol, isopropylmethylphenol, and the like. Examples of the pH adjuster include potassium carbonate, sodium hydrogen carbonate, hydrogencarbonate ammonium, and the like. Examples of the algefacient include L-menthol, camphor and the like.

Examples of the plant extract include extracts from *Poria cocos* Wolf, carrot, asian ginseng carrot, althea, *arnica, aloe,* nettle, fennel, Witchhazels, turmeric, Baikal skullcup, amur cork, *hypericum*, rice, adders-wort, camomile, *A. capillaries* Thunb, kiwi, cucumber, *lonicera, Sophora flavescens*, grapes, gardenia, watercress, Russian comfrey, soapwort, cactus, *Crataegus*, pehmn, Japanese basil, peony, Japanese white birch, *Equisetum arvense*, lime tree, *salvia, swertia kaponica, Cnidium officinale*, nulberry, soybean, *Thymus vulgaris, Angelica acutiloba, Calendula officinale*, Korean huttuynia, jujube, elder, parsley, Adlay, Bucharsbroom, loofah, cattail, hop, *Aesculus hippocastanum, Melissa officinalis*, peach, strawberry geranium, raspberry, lavender, Chinese milk vetch, rose, polyantha, rosemary, licorice, tea, lily, barley, wheat, *Angelica keiskei*, apricot, oat, corn, *mauritiana Malva, Lithospermum erythrorhizon*, chili pepper, ginger, lettuce, lemon, quince, orange, strawberry, safflower, fagaceae, *Gentiana lutea*, gentian, mint, *Mentha viridis, Mentha piperita*, soapberry, *eucalyptus, malva sylvestris, Sasa veitchii*, Astarm sile, *Asiasarum heterotropoide*, dead nettle, burdock, garlic, Sweet White Lupine, carob, pine, Japanese ivy, *Rodgersia podophylla*, burnet, kobotanzuru, meadowsweet, avocado, plant worm, sea onion, grapefruit, prune, lime, *Geranium thunbergii*, shiitake mushroom, Ononis, *potentilla tormentilla*, Chinese lemon, coptis, Japanese cypress, moutan, *ophiopogon planiscapus*, olive, sunflower, jojoba, macadamia nut, Meadowfoam, *camellia*, almond, cacao, sesame, Shea, borage, asparagus, madder, grape seed, *Mallotus japonicus*, akebia, *cannabis*, morning glory, azuki bean, cube gambir, *Hydrangea servata, Gynostemma pentaphyllum*, Japanese knotweed, fig, gingko, ylang-ylang, prunella, Japanese apricot, uva-ursi, *Citrus unshiu*, Siberuan ginseng, sickle senna, sophora, *pisum sativum*, psyllium, okra, elecampane, Japanese walnut, Valerianaceae, Fragaria, persimmon, ground ivy, cashew, valerian, snake gourd, Chinese quince, guarana, bellflower, mum, *Catalpa ovata*, Common Sorrel, *Gymnema sylvestre*, agrimony, guava, boxthorn, kuzu vine, camphor tree, chestnut, *Millettia reticulata*, laurel, Cinnamomi Cortex, *Rubus chingii*, pepper, coffee, figwort, *Jateorhiza columba*, sasanqua, Japanese pepper, saffron, Japanese cherry, pomegranate, *Sophora subprostrata, Cassia nomame*, aster, calamus, watermelon, *stevia*, plum, English ivy, pear, *Achillea millefolium*, juniper, horseradish, grassy-leaved sweet flag, Japanese parsley, senega, *senna*, pieplant, Daidai, tamarind, Japanese angelica tree, dandelion, chicory, clove, *Schisandra chinensis, Polyporus Sclerotium, oenothera tetraptera*, hydrocotyl, dayflower, *Tetragonia*, Persian walnut, winter melon, *Euconmia ulmoides*, Aibika, shepherd's-purse, Watson pomelo, nandina, bitterwood, fernleaf yarrow, pineapple, *hibiscus*, papaya, basil, lotus, Naked Barley, blackberry lily, peanut, *Rabalosia japonica*, water chestnut, pistachio, *Thujopsis dolabrata, Agaricus*, juniper, Japanese medlar, coltsfoot, *Rhus javanica*, boneset, blueberry, parsnip, Chinese lantern plant, Japanese big-leaf magnolia, Japanese quince, Turkestan rose, ephedra, mango, *Ganoderma lucidum, Bupleurum scorzonerifolium*, loosestrife, honewort, *mimosa*, melilot, melon, *magnolia, Momordica grosuenorii*, mulukhiya, malt, *Alpinia oxyphylla*, Leonuri Herba, *Rodgersia podophylla*, palm, Japanese green alder, mistletoe, water pepper, Pokeweed, bayberry, *Daphniphyllum macropodum, artemisia*, rye, orchid, longan, apple, lycee, *forsythia* and the like.

Examples of the whitening agent include glabridin, glabrene, liquiritin, isoliquiritin, hydroquinone and derivatives thereof, resorcin and derivatives thereof, glutathione, and the like. Examples of the blood circulation promoter include nonyl acid warenylamide, capsaicin, zingerone, Cantharides Tincture, ichthammol, α-borneol, inositolhexanicotinate, cyclandelate, cinnarizinee, tolazoline, acetylcholine, verapamil, γ-oryzanol, cepharanthine, and the like. Examples of the skin astringment include tannic acid and the like. Examples of the antiseborrheic agent include sulfur, thianthrol, and the like. Examples of the anti-inflammatory agent include mefenamic acid, phenylbutazone, indomethacin, ibuprofen, ketoprofen, allantoin, guaiazulene, ε-aminocaproic acid, diclofenac sodium, tranexamic acid, and the like. Examples of the active oxygen elimination agent include Superoxide dismutase, bilirubin, quercetin, quercetin, catechin, catechin derivative, gallic acid and derivatives thereof, and the like. Examples of the antioxidant include dibutylhydroxytoluene, butylhydroxyanisole, and the like. Examples of the enzyme include lipase, papain, and the like. Examples of the thickener (excluding thickener for the modified clay mineral and emulsion composition of the present invention) include 12-hydroxystearic acid, dextrin palmitate, N-acyl-L-amino acid alkylamide, and the like.

Other features of the invention will become apparent in the course of the following descriptions of exemplary embodiments which are given for illustration of the invention and are not intended to be limiting thereof.

EXAMPLES

Evaluation Methods

Emulsion Stability.

A B-type (Brookfield type) viscometer (manufactured by TOKYO KEIKI, DIGITAL VISCOMETER DVL-B) was used. About 100 ml of each emulsion composition was placed in a glass vial container, a rotor was appropriately selected, and the value obtained at a room temperature condition of 25° C., number of rotation of 6 or 60 rpm after 30 seconds was taken as the measurement value at each number of rotation. The measurement value at 60 rpm was divided by the measurement value at 6 rpm, and 0.10 to 0.19 was rated as ⊙, 0.20 to 0.29 was rated as ○, 0.30 to 0.39 was rated as Δ, and not less than 0.40 was rated as x.

Moisture Retention Property.

Moisture retention property was evaluated by the following procedures.

1) Set Up

A panelist is made to sit quietly on a chair in a room of at a temperature 21° C. and humidity 40% (error about 5%) for 30 min to acclimatize the subject to the environment.

2) Application Method of Emulsion Composition

Accurately measure 20 μl of each emulsion composition with a micropipetter, and apply the composition with a finger within a 2 cm radius circle on the skin of the panelist at a flexor part of the forearm (preferably at a center of a hairless part between the base of the palm and the articular of the arm).

3) Measurement Method of Skin Moisture

The skin moisture content before application, and 10 minutes and 30 minutes after application were measured using a skin moisture measuring machine SKICON 200 (manufactured by I.B.S Co., Ltd.). To be specific, a measuring apparatus (probe) is lightly pressed against the skin, the number is read after 5 seconds, and the average of 3 measurements is calculated and taken as the measurement value at each timing.

4) Evaluation Method of Moisture Retention Property

The measure of skin moisture content (30 minutes after application) is divided by the measure of skin moisture content (before application) to give the numerical value of moisture retention property, where not less than 2.4 is rated as ⊙, 2.3 to 2.0 is rated as ○, 1.9 to 1.6 is rated as Δ, and not more than 1.5 is rated as x.

Skin Irritation.

Each emulsion composition is applied to the skin of 5 panelists, and evaluated by them according to the following criteria.

4: feel no skin irritation at all
3: hardly feel skin irritation
2: slightly feel skin irritation
1: clearly feel skin irritation Based on the average score of the obtained numerical values, not less than 3.0 is rated as ⊙, 2.9 to 2.5 is rated as ○, 2.4 to 2.0 is rated as Δ, and not more than 1.9 is rated as x.

The starting materials used in the Examples are as follows.

(1) bentonite (clay mineral): manufactured by HOJUN Co., Ltd. "Bengel (trade name)", (2) montmorillonite (clay mineral): manufactured by KUNIMINE INDUSTRIES CO., LTD. "Kunipia G4"

(3) cocoylarginine ethyl pyrrolidone carboxylate: manufactured by Ajinomoto Co., Inc. "CAE (trade name)", (4) stearyltrimethylammonium chloride (quaternized ammonium salt type cationic surfactant): manufactured by Kao Corporation "Cortamine D86P (trade name, 63% solution)", (5) dodecamethylcyclohexasiloxane (silicone oil): "manufactured by Dow Corning Toray Silicone Co., Ltd. "DC246 (trade name)", (6) polyoxyethylene-methylpolysiloxane copolymer (non-ionic surfactant): manufactured by Nihon Emulsion Co., Ltd. "Emalex SS-5050K (trade name)", (7) fine particles titanium oxide (UV protecting agent): manufactured by TAYCA CORPORATION "titanium oxide MT-01 (trade name)", (8) isocetyl isostearate (ester oil): manufactured by Kokyu Alcohol Kogyo Co., Ltd. "ICIS (trade name)", (9) natural vitamin E (antioxidant): manufactured by Eisai Co., Ltd. "E Mix 70L (trade name)",

(10) self-emulsifying type glycerol monostearate (non-ionic surfactant): manufactured by Nihon Emulsion Co., Ltd. "Emalex GMS-50 (trade name)",

(11) dextrin palmitate (thickener): manufactured by Chiba Flour Milling Co., Ltd. "Leopal KL (trade name)",

(12) L-proline (moisturizing agent): manufactured by Ajinomoto Co., Inc.

(13) phenoxyethanol S (antibacterial agent): manufactured by Lion Corporation

(14) N-lauroyl-L-glutamic acid di(phytosteryl•behenyl•octyldodecyl) (moisturizing agent): manufactured by Ajinomoto Co., Inc. "Eldew (registered trade mark) PS-304"

Preparation of Modified Clay Mineral.

Preparation Example 1

A mixture of purified water and bentonite (45:5 mass ratio), and a mixture of purified water and cocoylarginine ethyl pyrrolidone carboxylate (45:5 mass ratio) were mixed and stirred to give a modified bentonite liquid (10 percent by mass).

Preparation Example 2

A mixture of purified water and montmorillonite (45:5 mass ratio), and a mixture of purified water and cocoylarginine ethyl pyrrolidone carboxylate (45:5 mass ratio) were mixed and stirred to give a modified bentonite liquid (10 percent by mass).

Preparation Example 3

Comparison

A mixture of purified water and bentonite (45:5 mass ratio), and a mixture of purified water and stearyltrimethylammonium chloride (42.05:7.95 mass ratio) were mixed and stirred to give a modified bentonite liquid (comparison). Preparation of Emulsion Compositions.

Examples 1-6 and Comparative Examples 1-3

Respective starting materials were mixed following the compositions shown in Table 1 to give W/O emulsion compositions (sunscreen preparations) of Examples 1-6 and Comparative Examples 1-3, and the evaluation results are summarized in Table 1.

Using various compounds instead of cocoylarginine ethyl ester, emulsion compositions similar to those in Example 1 were prepared. The emulsion stability was evaluated and summarized in Table 2.

TABLE 2

|  |  | R2 | | | |
| --- | --- | --- | --- | --- | --- |
|  |  | ethyl group | isopropyl group | isobutyl group | s-butyl group |
| R1 | lauric acid residue | ⊙ | ⊙ | ⊙ | ⊙ |
|  | palmitic acid residue | ⊙ | ○ | ○ | ○ |
|  | stearic acid residue | ⊙ | ○ | ○ | ○ |
|  | oleic acid residue | ⊙ | ○ | ○ | ○ |
|  | linoleic acid residue | ⊙ | ○ | ○ | ○ |
|  | coconut oil fatty acid residue | ⊙ | ⊙ | ⊙ | ⊙ |
|  | palm oil fatty acid residue | ⊙ | ○ | ○ | ○ |

TABLE 1

|  | Component Name | Ex. 1 | Ex. 2 | Ex. 3 | Ex. 4 | Ex. 5 | Ex. 6 | Comp. Ex. 1 | Comp. Ex. 2 | Comp. Ex. 3 |
| --- | --- | --- | --- | --- | --- | --- | --- | --- | --- | --- |
|  | dodecamethylcyclohexasiloxane | 35.00 | 35.00 | 35.00 | 35.00 | 35.00 | 35.00 | 35.00 | 35.00 | 35.00 |
|  | polyoxyethylene•methylpolysiloxane copolymer | 2.00 | 2.00 | 2.00 | 2.00 | 2.00 | 2.00 | 2.00 | 2.00 | 2.00 |
|  | fine particles titanium oxide | 5.00 | 5.00 | 5.00 | 5.00 | 5.00 | 5.00 | 5.00 | 5.00 | 5.00 |
|  | isocetyl isostearate | 15.00 | 15.00 | 15.00 | 15.00 | 15.00 | 15.00 | 15.00 | 15.00 | 15.00 |
|  | natural vitamin E | 0.10 | 0.10 | 0.10 | 0.10 | 0.10 | 0.10 | 0.10 | 0.10 | 0.10 |
|  | self-emulsifying type glycerol monostearate | 0.10 | 0.10 | 0.10 | 0.10 | 0.10 | 0.10 | 0.10 | 0.10 | 0.10 |
| Prep. Ex. 1 | 10 percent by mass modified bentonite solution | 4.00 | 9.00 | 16.00 | 4.00 | 9.00 | — | — | — | — |
| Prep. Ex. 2 | 10 percent by mass modified montmorillonite solution | — | — | — | — | — | 9.00 | — | — | — |
| Prep. Ex 3 (comparison) | 10 percent by mass modified bentonite solution (comparison) | — | — | — | — | — | — | — | 9.00 | 9.00 |
|  | palmitic acid dextrin | — | — | — | 0.40 | — | — | — | — | — |
|  | purified water | 38.55 | 33.55 | 26.55 | 38.15 | 33.35 | 33.36 | 42.55 | 33.55 | 33.55 |
|  | L-proline | — | — | — | — | 0.20 | — | — | — | 0.20 |
|  | magnesium sulfate | 0.10 | 0.10 | 0.10 | 0.10 | 0.10 | 0.10 | 0.10 | 0.10 | 0.10 |
|  | phenoxyethanol S | 0.15 | 0.15 | 0.15 | 0.15 | 0.15 | 0.15 | 0.15 | 0.15 | 0.15 |
| rotor number of rotation | 60 rpm | 125 | 191.9 | 352.4 | 145.7 | 205 | 1280(*) | 88.2 | 127.2 | 130 |
|  | 6 rpm | 342 | 681 | 1700 | 421 | 695 | 8600(*) | 183 | 250 | 255 |
| emulsion stability | (=60 rpm viscosity/6 rpm viscosity) | Δ(0.37) | ○(0.28) | ○(0.21) | Δ(0.35) | ○(0.29) | ⊙(0.15) | X(0.48) | X(0.51) | X(0.51) |
| skin water content (μS) | before application | ND | 34 | ND | ND | 41 | ND | ND | 33 | 38 |
|  | 10 min after application | ND | 85 | ND | ND | 112 | ND | ND | 66 | 70 |
|  | 30 min after application | ND | 75 | ND | ND | 97 | ND | ND | 49 | 53 |
| moisture retention property | (=value at 30 min after application/value before application) | ND | ○(2.21) | ND | ND | ⊙(2.4) | ND | ND | X(1.5) | X(1.4) |
| Skin irritation |  | ⊙ | ⊙ | ⊙ | ⊙ | ⊙ | ⊙ | ⊙ | X | X |

(*)No. 3 rotor was used. (No. 2 rotor was used for other Examples.)
ND: not detected By comparison with Comparative Example 1 free of modified clay mineral, an apparent thickening effect was observed in the quaternized ammonium modified clay minerals. However, the skin irritation was also observed, the moisture retention property was poor, and the emulsion stability was hardly improved (see, Comparative Examples 2 and 3).

It is clear that the emulsion composition of the present invention provides extremely remarkable effects such as superior emulsion stability, high moisture retention property and rare skin irritation, even when a comparatively small amount thereof is added (see, Examples 1-6).

It is clear that these acylargininealkyl esters have the same level of emulsion stabilizing effect as does cocoylarginine ethyl ester.

Examples 7-9

The emulsion compositions shown in Examples 7 to 9 were prepared according to the compositions shown in Table 3, and further adding acyl acidic amino acid ester as a moisturizing agent.

TABLE 3

| component name | Example 7 | Example 8 | Example 9 |
|---|---|---|---|
| dodecamethylcyclohexasiloxane | 35.00 | 35.00 | 35.00 |
| polyoxyethylene•methylpolysiloxane copolymer | 2.00 | 2.00 | 2.00 |
| fine particles titanium oxide | 5.00 | 5.00 | 5.00 |
| isostearic acid isocetyl | 15.00 | 15.00 | 15.00 |
| natural vitamin E | 0.10 | 0.10 | 0.10 |
| N-lauroyl-L-glutamic acid di(phytosteryl•behenyl•octyl-dodecyl) | 0.10 | 0.10 | 0.10 |
| self-emulsifying type glycerol monostearate | 0.10 | 0.10 | 0.10 |
| 10% modified bentonite solution | 4.00 | 9.00 | 16.00 |
| purified water | 38.45 | 33.45 | 26.45 |
| magnesium sulfate | 0.10 | 0.10 | 0.10 |
| phenoxyethanol S | 0.15 | 0.15 | 0.15 |

The emulsion compositions of Examples 7 to 9 show, in addition to the properties shown by the emulsion compositions of Examples 1 to 3, superior moisture retention property.

Examples 10-12

The components other than a modified clay mineral for constituting an emulsion composition, a clay mineral before modification in an oil layer, and cocoylarginine ethyl ester in an aqueous layer were mixed to form a modified clay mineral in the system, whereby the emulsion compositions of Examples 10 to 12 were prepared.

TABLE 4

| component name | Ex. 1 | Ex. 2 | Ex. 3 | Ex. 10 | Ex. 11 | Ex. 12 |
|---|---|---|---|---|---|---|
| dodecamethylcyclo-hexasiloxane | 35.00 | 35.00 | 35.00 | 35.00 | 35.00 | 35.00 |
| polyoxyethylene•methyl-poly siloxane copolymer | 2.00 | 2.00 | 2.00 | 2.00 | 2.00 | 2.00 |
| fine particles titanium oxide | 5.00 | 5.00 | 5.00 | 5.00 | 5.00 | 5.00 |
| isostearic acid isocetyl | 15.00 | 15.00 | 15.00 | 15.00 | 15.00 | 15.00 |
| natural vitamin E | 0.10 | 0.10 | 0.10 | 0.10 | 0.10 | 0.10 |
| self-emulsifying type glycerol monostearate | 0.10 | 0.10 | 0.10 | 0.10 | 0.10 | 0.10 |
| bentonite | | | | 0.4 | 0.9 | 1.6 |
| 10% modified bentonite solution | 4.00 | 9.00 | 16.00 | | | |
| purified water | 38.45 | 33.45 | 26.45 | 41.75 | 40.75 | 39.35 |
| cocoylarginine ethyl ester | | | | 0.4 | 0.9 | 1.6 |
| magnesium sulfate | 0.10 | 0.10 | 0.10 | 0.10 | 0.10 | 0.10 |
| phenoxyethanol S | 0.15 | 0.15 | 0.15 | 0.15 | 0.15 | 0.15 |

The emulsion compositions of Examples 10 to 12 showed similar properties as the emulsion compositions of Examples 1 to 3.

INDUSTRIAL APPLICABILITY

A modified clay mineral having emulsion stability, hardly showing skin irritation, and having moisture retention property, and further, an emulsion composition, a skin external preparation and various cosmetics such as hair cosmetic and the like, which contain the modified clay mineral, show emulsion stabilizing effect, hardly cause skin irritation, and have moisture retention property can now be obtained Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for making a modified clay mineral, comprising treating a clay mineral with a compound represented by formula (1):

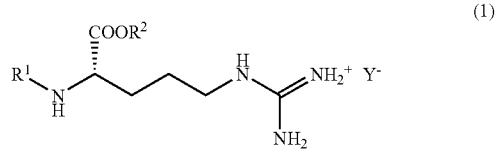

wherein $R^1$ is an acyl group, $R^2$ is an alkyl group, and $Y^-$ is an anion derived from an organic acid or an inorganic acid,
wherein said treating comprises:
(a) dissolving or dispersing said clay mineral and said compound of formula (1) in water, to obtain a solution or dispersion; and
(b) stirring said solution or dispersion to obtain said modified clay mineral,
wherein said clay mineral is treated with said compound represented by formula (1) in a weight ratio of said compound represented by formula (1) to said clay mineral of 1:10 to 10:1.

2. The process of claim 1, wherein $R^1$ is a saturated or unsaturated, straight chain or a branched chain acyl group having 12 to 18 carbon atoms.

3. The process of claim 1, wherein $R^2$ is an alkyl group having 1 to 10 carbon atoms.

4. The process of claim 1, wherein $Y^-$ is an anion selected from the group consisting of citrate, lactate, glutamate, pyrrolidone carboxylate, aspartate, chloride, sulfate, and nitrate.

5. The process of claim 1, wherein said clay mineral is selected from the group consisting of smectite, bentonite, montmorillonite, saponite, and hectorite.

6. The process of claim 1, wherein said clay mineral is treated with said compound represented by formula (1) in a weight ratio of said compound represented by formula (1) to said clay mineral of 1:4 to 4:1.

7. A modified clay mineral, which is prepared by a process according to claim 1.

8. An emulsion composition, comprising
(a) a modified clay mineral according to claim 7;
(b) water; and
(c) an oil,
wherein said emulsion has a viscosity measured at 60 rpm and a viscosity measured at 6 rpm such that the ratio of said viscosity measured at 60 rpm and said viscosity measured at 6 rpm is 0.10 to 0.39, said viscosity being measured for a 100 ml sample of said emulsion composition at a temperature of 25° C. following 30 seconds of rotation at either 6 rpm or 60 rpm.

9. The emulsion composition of claim 8, which is a cosmetic composition.

10. The emulsion composition of claim 8, which further comprises an acyl acidic amino acid ester.

11. A process of making an emulsion, comprising:
(a) combining a modified clay mineral according to claim 7 with an oil,
wherein said emulsion has a viscosity measured at 60 rpm and a viscosity measured at 6 rpm such that the ratio of said viscosity measured at 60 rpm and said viscosity measured at 6 rpm is 0.10 to 0.39, said viscosity being measured for a 100 ml sample of said emulsion composition at a temperature of 25° C. following 30 seconds of rotation at either 6 rpm or 60 rpm.

12. A method of improving a property of an emulsion, comprising adding a modified clay mineral according to claim 7 to an emulsion, wherein said property is stability of said emulsion, skin irritation effect of said emulsion, or moisture retention effect of said emulsion.

* * * * *